United States Patent [19]

Brown

[11] Patent Number: 4,523,015

[45] Date of Patent: Jun. 11, 1985

[54] PROCESS AND NITROAMINOPYRIMIDONE INTERMEDIATES FOR HISTAMINE $H_2$-ANTAGONISTS

[75] Inventor: Thomas H. Brown, Welwyn Garden City, England

[73] Assignee: Smith Kline & French Laboratories Limited, Welwyn Garden City, England

[21] Appl. No.: 151,502

[22] Filed: May 19, 1980

Related U.S. Application Data

[62] Division of Ser. No. 27,543, Apr. 6, 1979, Pat. No. 4,227,000.

[30] Foreign Application Priority Data

Apr. 11, 1978 [GB] United Kingdom ............... 14049/78

[51] Int. Cl.³ .............................................. C07D 401.12
[52] U.S. Cl. ...................................... 544/320; 544/238; 544/295; 544/296; 544/321
[58] Field of Search ................. 544/238, 295, 296, 320

[56] References Cited

U.S. PATENT DOCUMENTS

| | | | |
|---|---|---|---|
| 3,932,644 | 1/1976 | Durant et al. | 424/263 |
| 4,145,546 | 3/1979 | Brown et al. | 544/320 |
| 4,154,834 | 5/1979 | Brown et al. | 544/320 |
| 4,216,318 | 8/1980 | Brown et al. | 544/296 |
| 4,227,000 | 10/1980 | Brown | 544/238 |
| 4,305,945 | 12/1981 | Canellin et al. | 544/320 |

FOREIGN PATENT DOCUMENTS 2643670  4/1977  Fed. Rep. of Germany .
2658267  7/1977  Fed. Rep. of Germany .

*Primary Examiner*—Glennon H. Hollrah
*Assistant Examiner*—James H. Turnipseed
*Attorney, Agent, or Firm*—Joan S. Keps; Richard D. Foggio; Alan D. Lourie

[57] ABSTRACT

A process for making substituted 2-aminopyrimidones which are histamine $H_2$-antagonists which comprises reacting a 2-nitroaminopyrimidone with a heteroarylalkylamine, heteroarylalkylthioalkylamine, or heteroarylalkoxyalkylamine. One particular compound which can be made by this process is 2-[2-(5-methyl-4-imidazolylmethylthio)ethylamino]-5-[5-(1,3-benzodioxyolyl)methyl]-4-pyrimidone. Also claimed are 2-nitroaminopyrimidone intermediates for use in this process. One specific intermediate is 2-nitroamino-5-[5-(1,3-benzodioxyolyl)methyl]-4-pyrimidone.

10 Claims, No Drawings

PROCESS AND NITROAMINOPYRIMIDONE INTERMEDIATES FOR HISTAMINE H₂-ANTAGONISTS

This is a division of application Ser. No. 027,543 filed Apr. 6, 1979 now U.S. Pat. No. 4,227,000.

This invention relates to a chemical process for preparing 2-aminopyrimidones which have histamine $H_2$-antagonist activity, and to novel intermediates for use in this process.

In German Offenlegungsschriften Nos. 2643670 and 2658267 there are described specific processes for preparing 2-aminopyrimidones which comprise reacting an amine with a pyrimidone which has a lower alkylthio, benzylthio or halogen group in the 2-position. We have found that a better process for preparing these 2-aminopyrimidones is to react an amine with a pyrimidone which has a nitroamino group in the 2-position.

According to the invention there is provided a process for preparing a 2-aminopyrimidone of Structure 1:

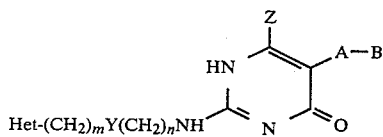
(1)

in which Het is a nitrogen-containing 5- or 6-membered fully unsaturated heterocyclic group which is optionally substituted by one or more lower alkyl, trifluoromethyl, halogen, hydroxy, lower alkoxy or amino groups which groups can be the same or different, m is 0 or 1, Y is methylene, oxygen or sulphur, n is 2 or 3; Z is hydrogen or lower alkyl (preferably methyl); A is $C_1$–$C_5$ alkylene or —$(CH_2)_p$—W$(CH_2)_q$— where W is oxygen or sulphur and the sum of p and q is 1 to 4 and B is hydrogen, methyl, $C_3$–$C_6$ cycloalkyl, a heteroaryl group optionally substituted by one or more (which may be the same or different) lower alkyl or lower alkoxy groups, or B is a naphthyl, 5- or 6-(2,3-dihydro-1,4-benzodioxinyl), or a 4- or 5-(1,3-benzodioxolyl) group, or a phenyl group optionally substituted with one or more (which may be the same or different) lower alkyl, lower alkoxy, halogen, aryl(lower alkoxy) (preferably benzyloxy), hydroxy, lower alkoxy-lower alkoxy, trifluoromethyl, di(lower alkyl)amino, phenoxy, halophenoxy, lower alkoxypheonxy, phenyl, halophenyl or lower alkoxyphenyl groups; characterised in that an amine of Structure 2, in which Het, m, Y and n are as defined for Structure 1, is reacted with a 2-nitroaminopyrimidone of Structure 3, in which Z, A and B are

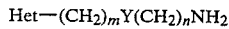
(2)

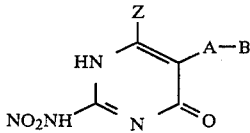
(3)

as defined for Structure 1. A phenolic hydroxy group can, if desired, be protected during the reaction and subsequently regenerated. Examples of hydroxy protecting groups are methoxymethyl, methylthiomethyl, tetrahydropyranyl, benzyl, acyl and lower alkyl.

Throughout this specification by the terms 'lower alkyl' and 'lower alkoxy' are meant alkyl and alkoxy groups which can be straight or branched and which contain 1 to 4 carbon atoms. Particular lower alkyl groups are methyl, ethyl, 1-propyl and 2-propyl. Particular lower alkoxy groups are methoxy, ethoxy, 1-propoxy and 2-propoxy.

Examples of heterocycles of the group Het are imidazole, pyridine, thiazole, isothiazole, oxazole, isoxazole, triazole and thiadiazole. Preferably the group Het is linked to $(CH_2)_m$ by a carbon atom of the heterocycle adjacent to a nitrogen atom. Examples of the group Het are 2- or 4-imidazolyl optionally substituted by lower alkyl (preferably methyl), halogen (preferably chlorine or bromine), trifluoromethyl or hydroxymethyl, 2-pyridyl optionally substituted by one or more (which can be the same or different) lower alkyl (preferably methyl), lower alkoxy (preferably methoxy), halogen (preferably chlorine or bromine), amino or hydroxy groups, 2-thiazolyl, 3-isothiazolyl optionally substituted by chlorine or bromine, 3-(1,2,5)-thiadiazolyl optionally substituted by chlorine or bromine, or 2-(5-amino-1,3,4-thiadiazolyl). Particular Het groups are 5-methyl-4-imidazolyl, 5-bromo-4-imidazolyl, 2-pyridyl, 3-methyl-2-pyridyl, 3-methoxy-2-pyridyl, 3-ethoxy-2-pyridyl, 3,4-dimethoxy-2-pyridyl, 3-fluoro-2-pyridyl, 3-chloro-2-pyridyl, 3-bromo-2-pyridyl, 3-iodo-2-pyridyl, 3-bromo-4-methyl-2-pyridyl and 2-thiazolyl.

Examples of heteroaryl groups B are pyridyl, furyl, thienyl, thiazolyl, oxazolyl, isothiazolyl, imidazolyl, pyrimidyl, pyrazinyl, pyridazyl, thiadiazolyl, quinolyl, isoquinolyl, 5,6,7,8-tetrahydroquinolyl, 1,3-dioxolopyridyl, benzimidaziolyl and benzthiazolyl. Particular heteroaryl groups are 2-furyl, 2-thienyl, 2-pyridyl, 3-pyridyl, 4-pyridyl, 2-thiazolyl, 2-imidazolyl, 2-pyrimidyl, 2-pyrazyl, 3-pyridazyl, 3-quinolyl and 1-isoquinolyl optionally substituted by one or more lower alkyl or lower alkoxy groups. Specific heteroaryl groups are 2-furyl, 3-pyridyl, 6-methyl-3-pyridyl, 5,6-dimethyl-3-pyridyl, 6-methoxy-3-pyridyl, 2-methoxy-4-pyridyl and 4-methoxy-2-pyridyl.

Specific substituted pheny groups B are 3-chlorophenyl, 3,4-dichlorophenyl, 3-methoxyphenyl, 4-methoxyphenyl, 3,4-dimethoxyphenyl and 3,4,5-trimethoxyphenyl.

Specific meanings of A are methylene, 1,1-ethanediyl (—CHCH₃—), 1,2-ethanediyl (—CH₂CH₂—), 1,3-propanediyl (—CH₂CH₂CH₂—) and oxymethyl (—OCH₂—).

The reaction can be carried out at an elevated temperature in the absence of a solvent, for example at 80° to 170°, preferably 120° to 140°, or in a solvent at an elevated temperature, for example at the reflux temperature of the reaction mixture. The choice of solvent is affected by solubility characteristics of the reactants. Preferably the solvent is pyridine, a picoline or mixture of picolines, a lower alkanol, preferably ethanol or 1-propanol, an aqueous mixture of a lower alkanol, 1,2-ethanediol, a ketone, for example acetone or 2-butanone, or a polar aprotic solvent, for example dimethylformamide, dimethylacetamide, dimethylsulphoxide, hexamethylphosphoramide, sulpholane, acetonitrile or nitromethane. Particularly preferably the reaction is carried out in refluxing ethanol, refluxing 1-propanol or refluxing pyridine.

Preferably approximately equimolar amounts of the reactants are used, although an excess, for example a slight excess of from 1.1 to 1.5 molar equivalents or a larger excess of from 1.5 to 4 molar equivalents, of either reactant can be used. If an excess of a reactant is used then preferably an excess of the amine of Structure 2 is used. An excess of either reactant can be present at the start of the reaction or can be added during the course of the reaction.

This invention provides a process for preparing compounds of a wide range of structures which have histamine H$_2$-antagonist activity. Many of the compounds of Structure 1 are described in German Offenlegungsschriften Nos. 2643670 and 2658267 as having histamine H$_1$- and H$_2$-antagonist activity and in U.S. Pat. No. 3,932,644 as having histamine H$_2$-antagonist activity. Histamine H$_2$-antagonists and compounds which have histamine H$_1$- and H$_2$-antagonist activity are useful as inhibitors of gastric acid secretion, as antiinflammatory agents and as agents which inhibit the effects of histamine on blood pressure.

The process of this invention is particularly useful for preparing compounds of Structure 1 in which Het is 2-thiazolyl, 5-methyl-4-imidazolyl, 5-bromo-4-imidazolyl, 3-bromo-2-pyridyl, 3-chloro-2-pyridyl, 3-methoxy-2-pyridyl or 3-hydroxy-2-pyridyl group, and in which m is 1 and n is 2.

Specifically the process is useful for preparing:
(a) 2-[2-(5-methyl-4-imidazolylmethylthio)ethylamino]-5-(3-methoxybenzyl)-4-pyrimidone
(b) 2-[2-(5-methyl-4-imidazolylmethylthio)ethylamino]-5-(5-(1,3-benzodioxolyl)methyl)-4-pyrimidone
(c) 2-[2-(5-methyl-4-imidazolylmethylthio)ethylamino]-5-(3-pyridylmethyl)-4-pyrimidone
(d) 2-[4-(3-methoxy-2-pyridyl)butylamino]-5-(6-methyl-3-pyridylmethyl)-4-pyrimidone and
(e) 2-[4-(3-methoxy-2-pyridyl)butylamino]-5-(3-pyridylmethyl)-4-pyrimidone The compounds of Structures 1 and 3 are shown and described as 4-pyrimidone derivatives and these derivatives exist in equilibrium with the corresponding 6-pyrimidone tautomers, and the pyrimidine ring may also exist in the following tautomeric forms:

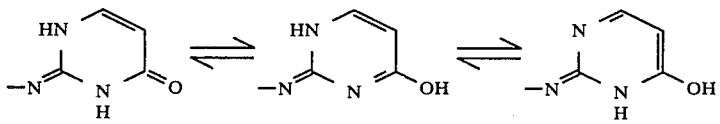

The process of this invention can in general be carried out at lower temperatures or at similar temperatures with shorter reaction times when compared with the process involving displacement of a methylthio group and in general gives the products in a purer state or in better yield. The intermediates of Structure 3 can be prepared more easily than the corresponding 2-methylthio-4-pyrimidones as the former compounds can be prepared directly from a β-oxoester without an alkylation step. This process which involves a 2-nitroamino-4-pyrimidone is advantageous when compared with the corresponding process involving a 2-methylthio-4-pyrimidone as with the former process one can use a salt of the amine of Structure 2, for example a hydrochloride, with one equivalent of a base, for example sodium ethoxide, whereas it has been found that the latter process does not proceed satisfactorily when a salt of the amine of Structure 2 and one equivalent of base are used.

The process of this invention is advantageous when compared to the corresponding process in which a lower alkylmercaptan or benzylmercaptan is displaced as the generation of volatile compounds with unpleasant odours is avoided. The displacement of a 2-nitroamino group generates water and nitrous oxide.

The process of this invention which uses a 2-nitroamino-4-pyrimidone is advantageous when compared with the corresponding process which uses a 2-halo-4-pyrimidone as a hydrohalic acid is generated during the latter reaction and this necessitates the addition of an additional base or the use of an excess of the amine of Structure 2, and the 2-halo-4-pyrimidone intermediates are more difficult to prepare as they require an additional diazotisation step.

The 2-nitroamino-4-pyrimidones of Structure 3 can be prepared by reacting a β-oxoester of Structure 4 (in which R is lower alkyl) with nitroguanidine. When Z is hydrogen the β-oxoester of Structure 4 can be used in the form of a hemiacetal of a lower alkanol.

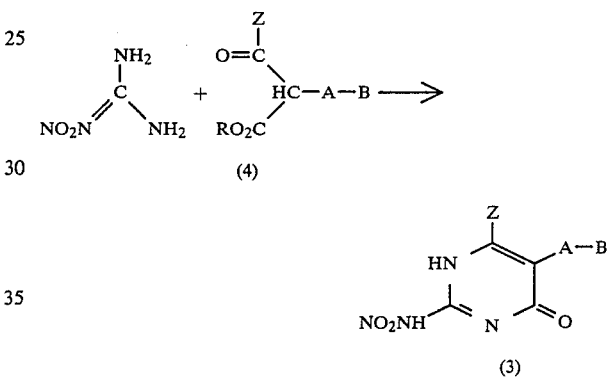

Preferably this reaction is carried out in the presence of a base, for example an alkali metal hydroxide or lower alkoxide, sodium hydride or a quaternary ammonium hydroxide, for example benzyltrimethylammonium hyroxide. Preferably the base is sodium hydroxide, sodium ethoxide or sodium methoxide, and preferably 2 molar equivalents of one of these bases is used. Preferably this reaction is carried out in a lower alkanol, for example, methanol, ethanol or 1-propanol, in an aqueous mixture of a lower alkanol, or in dimethylformamide. Preferably this reaction is carried out at an elevated temperature, for example the boiling point of the reaction mixture, but any temperature at which the reaction proceeds at an acceptable rate can be used. Nitroguanidine is usually sold in a wet state (for example containing 17 to 25% water by weight) and can be used in a wet or in a dry state.

The invention also provides new 2-nitroamino-4-pyrimidones of particular use in the process for making the compounds of Structure 1. These 2-nitroamino-4-pyrimidones are those of Structure 3 in which B is a heteroaryl group optionally substituted by one or more (which can be the same or different) of the groups lower alkyl and lower alkoxy, examples of which are set forth hereabove in the definition of B relating to Structure 1, or B is a naphthyl 5- or 6-(2,3-dihydro-1,4-benzodioxinyl), or a 4- or 5-(1,3-benzodioxolyl) group, or a phenyl group substituted with one or more (which can be the same or different) lower alkyl, lower alkoxy, halogen, aryl(lower alkoxy) (preferably benzyloxy), hydroxy, lower alkoxy-lower alkoxy, trifluoromethyl, di(lower alkyl)amino, phenoxy, halophenoxy, lower alkoxyphenoxy, phenyl, halophenyl or lower alkoxyphenyl groups. Preferably A is methylene and B is 3-pyridyl, 6-methyl-3-pyridyl, 5,6-dimethyl-3-pyridyl, 6-methoxy-3-pyridyl, 2-methoxy-4-pyridyl, 4-methoxy-2-pyridyl, 3-methoxyphenyl, 6-(2,3-dihydrobenzodioxinyl) or 5-(1,3-benzodioxolyl) as these intermediates give compounds of Structure 1 with particularly useful activity, and particularly preferably B is 6-methyl-3-pyridyl, 5,6-dimethyl-3-pyridyl or 6-methoxy-3-pyridyl. In general the intermediates of Structure 3 can be easily purified by recrystallisation and are stable when stored at room temperature.

The β-oxoesters of Structure 4 in which Z is hydrogen can generally be prepared by formulating an ester B-A-CH$_2$CO$_2$R with a lower alkyl formate, for example ethyl formate. and a strong base, for example sodium hydride in 1,2-dimethoxyethane or tetrahydrofuran, or by using sodium in ether. Preferably in this reaction at least 1.5 molar equivalents of ethyl formate are used. Preferably approximately two molar equivalents of sodium hydride are used. The β-oxoesters of Structure 4 can be used in an unpurified form for the reaction with nitroguanidine or in some cases can be isolated and used as crystalline solids. The β-oxoesters of Structure 4 in which Z is lower alkyl can be prepared by alkylating an acylacetate ester.

The invention is illustrated by the following Examples, which are preceded by Preparations of intermediates. All temperatures are in °C.

PREPARATION 1

(i) A mixture of 6-methylpyridine-3-carboxaldehyde (51.57 g), malonic acid (44.30 g), piperidine (6 ml) and pyridine (300 ml) was stirred at 100° for 3 hours and was allowed to cool. The mixture was evaporated to dryness, water was added to the residue and the solid was filtered off and recrystallised from ethanol-acetic acid to give 3-(6-methyl-3-pyridyl)acrylic acid (41.25 g), m.p. 213.5°–215.5°.

(ii) A stirred mixture of 3-(6-methyl-3-pyridyl)acrylic acid (50.70 g), dry ethanol (350 ml) and concentrated sulphuric acid (25 ml) was heated under reflux for 18 hours and ethanol (~250 ml) was removed by evaporation. The residue was poured into ice-aqueous ammonia and the mixture was extracted with ether. The ether extracts were washed with water and evaporated to an oil which crystallised on standing to give ethyl 3-(6-methyl-3-pyridyl)acrylate, m.p. 36°–37°.

(iii) Ethyl 3-(6-methyl-3-pyridyl)acrylate (60.36 g) was hydrogenated in ethanol at 35° and 355 kPa using palladium-on charcoal catalyst (10%, 1.0 g). The mixture was filtered and the filtrate was evaporated to give ethyl 3-(6-methyl-3-pyridyl)propionate as an oil.

(iv) A mixture of ethyl 3-(6-methyl-3-pyridyl)propionate (1.31 g) and ethyl formate (7.43 g) was added dropwise to a stirred suspension of sodium hydride (50% dispersion in oil, 4.07 g) in dry 1,2-dimethoxyethane (24 ml) maintained at 0°. The mixture was allowed to warm to room temperature, stirred overnight and poured into ice-water (300 g). The mixture was extracted with ether, the aqueous phase was adjusted to pH 5.4 with hydrochloric acid, and the solid which separated was collected to give ethyl 2-formyl-3-(6-methyl-3-pyridyl)propionate (10.5 g, 70%), m.p. 142°–4°.

PREPARATION 2

(i) A mixture of ethyl formate (111 g) and 2-butanone (108 g) was added dropwise to a stirred mixture of sodium hydride in oil (50% w/w, 72 g) in dry 1,2-dimethoxyethane and the mixture was allowed to stand overnight. Ether (800 ml) was added and the solid (101 g) was filtered off. Cyanoacetamide (69.5 g), piperidine acetate (prepared by adding piperidine to acetic acid (7 ml) and water (18 ml) until the mixture was basic) and water (400 ml) were added to this solid and the mixture was heated under reflux for 2 hours and allowed to cool. The mixture was acidified with acetic acid and the solid which precipitated out was recrystallised from aqueous ethanol to give 3-cyano-5,6-dimethyl-2-hydroxypyridine (43.5 g).

(ii) An intimate mixture of 3-cyano-5,6-dimethyl-2-hydroxypyridine (42 g) and phosphorus pentachloride (81 g) was heated at 140°–160° C. for 2 hours. Phosphoryl chloride was removed by distillation under reduced pressure and ice-water (500 g) was added to the residue. The mixture was adjusted to pH 7 with aqueous sodium hydroxide and extracted with ether. The ether extracts were evaporated to an oil which was crystallised from ether-light petroleum (b.p. 60°–80°) to give 2-chloro-3-cyano-5,6-dimethylpyridine (25.3 g), m.p. 83°–7°.

(iii) A mixture of 2-chloro-3-cyano-5,6-dimethylpyridine (21.5 g), semicarbazide hydrochloride (24.0 g), sodium acetate (42.3 g), water (225 ml) and methanol (475 ml) was hydrogenated at 344 kPa at 50° using Raney nickel catalyst (5 g). The mixture was added to water (750 ml) and filtered. The solid filtered off was suspended in water (130 ml) and concentrated hydrochloric acid (70 ml) was added and the mixture was heated at 100° for 1 hour; formalin (40% w/w, 120 ml) was added and the mixture was heated at 100° for a further 0.5 hour and allowed to cool. Sodium acetate (95 g) and water (250 ml) were added and the mixture was extracted with ether and the extracts were washed with 5% aqueous potassium carbonate and evaporated to give 2-chloro-5,6-dimethyl-3-pyridinecarboxaldehyde (13.24 g, 60%), m.p. 69°–70°.

(iv) A mixture of 2-chloro-5,6-dimethyl-3-pyridinecarboxaldehyde (16.85 g), malonic acid (11.45 g), piperidine (10 ml) and pyridine (100 ml) was heated under reflux for 1 hour and evaporated to an oil. This oil was dissolved in sodium hydroxide solution and was extracted with chloroform, the residual aqueous phase was acidified with hydrochloric acid and extracted with chloroform. The second chloroform extracts were washed with wafter and evaporated to give 3-(2-chloro-5,6-dimethyl-3-pyridyl)acrylic acid (18.3 g, 87%), m.p. 150°–8°. This acid was esterified using ethanol and sulphuric acid to give the ethyl ester, m.p. 85°–8°.

(v) The ethyl ester (32.7 g) in ethanol (500 ml) was hydrogenated at 25°–30° and 344 kPa using palladium-on-charcoal catalyst (5%, 3g). The mixture was filtered and the filtrate was evaporated to an oil which was partitioned between chloform and 2N hydrochloric acid. The aqueous phase was made basic with aqueous sodium hydroxide, extracted with chloroform and the chloroform extracts were evaporated to give ethyl 3-(5,6-dimethyl-3-pyridyl)propionate (21.8 g, 80%) as an oil.

(vi) Reaction of ethyl 3-(5,6-dimethyl-3-pyridyl)propionate with ethyl formate and sodium hydride in dimethoxyethane at room temperature gave ethyl 3-(5,6-dimethyl-3-pyridyl)-2-formylpropionate, m.p. 148°–9°.

PREPARATION 3

(i) 2-Chloro-4-cyanopyridine (115.5 g) in methanoldioxan (1:1, 850 ml) was added to a solution of sodium methoxide (prepared from 20.8 g sodium) in methanol (285 ml) and the mixture was heated under reflux for 2.5 hours and then allowed to cool. The mixture was filtered and the volume of the filtrate was reduced by evaporation to 200 ml and water (400 ml) was added. The solid which precipitated was filtered off to give 2-methoxy-4-cyanopyridine (57.2 g, 51%), m.p. 93°–95.5°.

(ii) A mixture of 2-methoxy-4-cyanopyridine (57.2 g), semicarbazide hydrochloride (71.24 g), sodium acetate (69.86 g), ethanol (1200 ml) and water (370 ml) was hydrogenated at 344 kPa using Raney nickel catalyst (1.0 g). The mixture was evaporated to a volume of 450 ml, water (900 ml) was added and the mixture was allowed to stand at 0° overnight. The mixture was filtered and the solid residue was washed with water and then dissolved in 10% hydrochloric acid (950 ml). Formaldehyde solution (36% w/v, 420 ml) was added and the mixture was warmed for 30 minutes, allowed to cool and added to a solution of sodium acetate (290 g) in water (840 ml). The mixture was extracted with ether and the combined extracts were successively washed with aqueous potassium carbonate and water and were dried and evaporated to give 2-methoxypyridine-4-carboxaldehyde (20.53 g, 35%), m.p. 33°–35°. A sample recrystallised from light petroleum had m.p. 33°–36°.

(iii) Condensation of 2-methoxypyridine-4-carboxaldehyde with malonic acid with subsequent esterification and hydrogenation at 344 kPa and formylation of the product with ethyl formate and sodium hydride gave ethyl 2-formyl-3-(2-methoxy-4-pyridyl)propionate as an oil.

PREPARATION 4

Substitution of 4-methoxypyridine-2-carboxaldehyde for 2-methoxypyridine-4-carboxaldehyde in the procedure of Preparation 3 gave ethyl 3-(4-methoxy-2-pyridyl)propionate as an oil which was formylated to give ethyl 2-formyl-3-(4-methoxy-2-pyridylmethyl)-pyrimidone.

PREPARATION 5

(i) A mixture of 2-methoxy-5-cyanopyridine (61.26 g), semicarbazide hydrochloride (76.4 g), sodium acetate (74.92 g), ethanol (1300 ml) and water (400 ml) was hydrogenated at 344 kPa using Raney nickel catalyst (1.0 g). The mixture was evaporated to a volume of 500 ml, water (1000 ml) was added and the mixture was allowed to stand at 0° overnight. The mixture was filtered and the solid was washed with water and dissolved in 10% hydrochloric acid (1000 ml). Formaldehyde solution (36% w/v, 450 ml), was added and the mixture was warmed for 15 minutes, allowed to cool and was added to a solution of sodium acetate (298.5 g), in water (900 ml). This mixture was extracted with ether (3×500 ml) and the combined extracts were successively washed with aqueous potassium carbonate and water and were dried and evaporated to give 6-methoxy-pyridine-3-carboxaldehyde (31.5 g, 50%), m.p. 48°–9°.

(ii) A mixture of 6-methoxypyridine-3-carboxaldehyde (2.34 g), monoethyl malonate (4.51 g), pyridine (12 ml) and piperidine (6 drops) was heated under reflux for 5 hours and was evaporated to an oil. This oil was partitioned between ether and dilute aqueous ammonia. The separated ether layer was washed with water and evaporated to an oil which crystallised on standing to give ethyl 3-(6-methoxy-3-pyridyl)acrylate (2.8 g, 79%), m.p. 49°–52°.

(iii) Ethyl 3-(6-methoxy-3-pyridyl)acrylate (32.33 g), in ethanol (160 ml) was hydrogenated at 344 kPa at 40° using palladium-on-charcoal catalyst (5%, 0.2 g). The mixture was filtered and the filtrate was evaporated to give ethyl 3-(6-methoxy-3-pyridyl)propionate (32.7 g), as an oil.

(iv) A mixture of ethyl 3-(6-methoxy-3-pyridyl)propionate (32.74 g), and ethyl formate (17.22 g), was added dropwise over 1.5 hours to a stirred suspension of sodium hydride in oil (50%, 9.38 g), in 1,2-dimethoxyethane (50 ml) cooled to −2°, allowed to stand overnight at room temperature and then poured on to ice. The mixture was extracted with ether and the aqueous phase was adjusted to pH 5 with 2N sulphuric acid. An oil was precipitated and crystallised on standing to give ethyl 2-formyl-3-(6-methoxy-3-pyridyl)propionate (25.9 g, 70%), m.p. 91.5°–94°. A sample recrystallised from aqueous ethanol had m.p. 93°–4°.

PREPARATION 6

Ethyl 3-(2-furyl)propionate was reacted with 1.1 equivalents ethyl formate and 1.0 equivalents sodium hydride in 1,2-dimethoxyethane at room temperature to give ethyl 2-formyl-3-(2-furyl)propionate as an oil in 75% yield.

PREPARATION 7

A mixture of ethyl 3-(3-methoxyphenyl)propionate (100 g) and ethyl formate (37 g) was added dropwise to a mixture of sodium wire (11 g) in stirred ether (500 ml) at 0°. The mixture was stirred at room temperature for 16 hours and evaporated to dryness. The residue was dissolved in water and extracted with ether, the extracted aqueous phase was adjusted to pH 4 with hydrochloric acid and was extracted with ether and the ether extract was evaporated to dryness to give ethyl 2-formyl-3-(3-methoxyphenyl)propionate (46.05 g).

PREPARATION 8

Ethyl 3-(3,4,5-trimethoxyphenyl)propionate was reacted with ethyl formate and sodium hydride in 1,2-dimethoxyethane to give crude ethyl 2-formyl-3-(3,4,5-trimethoxyphenyl)propionate in 44% yield.

PREPARATION 9

2,3-Dihydro-1,4-benzodioxin-6-carboxaldehyde (m.p. 41°–43°, prepared by reacting 3,4-dihydroxybenzaldehyde with ethanedisulphonic acid dimethyl ester and potassium hydroxide) was condensed with monoethyl malonate in pyridine with piperidine as catalyst to give ethyl 3-(6-(2,3-dihydro-1,4-benzodioxinyl)acrylate, m.p. 49°–53°, which was reduced with hydrogen and palladium-on-charcoal, and the product was reacted with ethyl formate and sodium hydride in 1,2-dimethoxyethane to give ethyl 2-formyl-3-[6-(2,3-dihydro-1,4-benzodioxinyl)]propionate as an oil.

PREPARATION 10

A mixture of ethyl 3-(1-naphthyl)propionate (18.01 g) and ethyl formate (8.88 g) was added to a suspension of sodium hydride (57% dispersion in oil, 4.43 g) in 1,2-dimethoxyethane stirred at 5°, and the mixture was stirred at 5° for one hour and allowed to warm to room temperature. Water (300 ml) was added and the mixture was extracted with chloroform and the residual aqueous phase adjusted to pH 4 with hydrochloric acid: the mixture was extracted with ether and the extracts evaporated to give ethyl 2-formyl-3-(1-naphthyl)propionate (16.05 g) as an oil.

PREPARATION 11

(i) A solution of sodium methoxide (from 0.535 g sodium) in dry methanol (40 ml) was added dropwise to a stirred suspension of 3-fluoro-2-methyl-4-nitropyridine N-oxide (2 g) in dry methanol (50 ml) and the mixture was stirred overnight. Additional sodium methoxide (from 0.053 g sodium) was added and the mixture was heated under reflux for 1 hour. The mixture was neutralised with hydrochloric acid and evaporated to dryness. The residue was extracted with chloroform and the extract was evaporated to dryness to give 3,4-dimethoxy-2-methylpyridine N-oxide.

(ii) Trifluoroacetic anhydride (4.0 ml) was added dropwise to a stirred solution of 3,4-dimethoxy-2-methylpyridine N-oxide (1.91 g) in dichloromethane (25 ml) and the mixture was left to stand at room temperature for 8 days during which time trifluoroacetic anhydride (4.77 ml) was added in two portions. The mixture was evaporated to dryness and the residue was purified by extracting a chloroform solution with aqueous sodium bicarbonate and elution from silica gel with methanol-chloroform (1:9) to give 2-hydroxymethyl-3,4-dimethoxypyridine (1.6 g).

(iii) 2-Hydroxymethyl-3,4-dimethoxypyridine was reacted with thionyl chloride in chloroform to give 2-chloromethyl-3,4-dimethoxypyridine hydrochloride, m.p. 158°–9° (decomp), which was reacted with cysteamine hydrochloride and sodium ethoxide in ethanol to give 2-(3,4-dimethoxy-2-pyridylmethylthio)ethylamine.

EXAMPLE 1

Sodium (1.15 g) was dissolved in methanol (50 ml) and nitroguanidine (4.7 g) was added to the cooled solution. The mixture was heated under reflux for 45 minutes, ethyl 2-formyl-3-(3-pyridyl)propionate (9.3 g) was added portionwise and the mixture was heated under reflux for 45 hours and evaporated to dryness. Water was added to the residue and the mixture was extracted with chloroform. The residual aqueous phase was adjusted to pH 5 with acetic acid, and the solid which was precipitated was filtered off, washed and dried to give 2-nitroamino-5-(3-pyridylmethyl)-4-pyrimidone, m.p. 214.5°–216°, in 38% yield.

EXAMPLE 2

A solution of ethyl 2-formyl-3-(6-methyl-3-pyridyl)propionate (1.55 g) in methanol (20 ml) was added to a stirred solution of sodium methoxide (from 0.161 g sodium) in methanol (20 ml). Dried nitroguanidine (0.73 g) was added and the mixture was heated under reflux overnight and evaporated to dryness. The residue was dissolved in water (50 ml) and the solution was extracted with chloroform and the aqueous phase was adjusted to pH 5 with acetic acid. The solid which precipitated was filtered off and recrystallised from methanol-acetic acid to give 2-nitroamino-5-(6-methyl-3-pyridylmethyl)-4-pyrimidone (0.5 g, 27%), m.p. 215°–6° (decomp).

EXAMPLE 3

Nitroguanidine (6.05 g) was added to a solution of sodium methoxide (prepared from 1.45 g sodium) in dry methanol (65 ml) and the mixture was heated under reflux for 0.75 hours. Ethyl 3-(5,6-dimethyl-3-pyridyl)-2-formylpropionate (14.3 g) was added and the mixture was heated under reflux for 40 hours and evaporated to dryness. Water (40 ml) was added to the residue and the mixture was extracted with chloroform. The aqueous phase was adjusted to pH 6 with hydrochloric acid and the solid which separated was filtered off and recrystalised from dimethylformamideethanol to give 5-(5,6-dimethyl-3-pyridylmethyl)-2-nitroamino-4-pyrimidone, m.p. 212°–3°.

EXAMPLE 4

When nitroguanidine was reacted with sodium ethoxide and ethyl 3-(4-methoxy-2-pyridyl)propionate in a process similar to that described in Example 3, there was obtained 2-nitroamino-5-(4-methoxy-2-pyridylmethyl)pyrimidone, m.p. 196°–8° (decomp), (from ethanol-acetic acid).

EXAMPLE 5

Nitroguanidine (4.7 g) was added to a solution of sodium methoxide (prepared from 1.15 g sodium) in methanol (50 ml) and the mixture was heated under reflux for 45 minutes. Ethyl 2-formyl-3-(6-methoxy-3-pyridyl)propionate (10.7 g) was added and the mixture was heated under reflux for 24 hours and evaporated to dryness. The residue was dissolved in water and the solution was extracted with chloroform. The residual aqueous solution was adjusted to pH 5 with acetic acid, and the solid which precipitated was filtered off to give 2-nitroamino-5-(6-methoxy-3-pyridylmethyl)-4-pyrimidone, m.p. 183.5°–186°.

EXAMPLE 6

By a process similar to that of Example 5, reaction of nitroguanidine, sodium methoxide and ethyl 2-formyl-3-(2-methoxy-4-pyridyl)-propionate gave 2-nitroamino-5-(2-methoxy-4-pyridyl)-4-pyrimidone, m.p. 194°–5.5° (from aqueous acetic acid).

EXAMPLE 7

Ethyl 2-formyl-3-(2-furyl)propionate (24.0 g, 0.122 mol) was added to a mixture of nitroguanidine (12.69 g, 0.122 mol) and sodium methoxide (from 3.09 g, 0.134 mol, sodium) in methanol and the mixture was stirred and heated under reflux for 18 hours and evaporated to dryness. The residue was dissolved in water and the solution was adjusted to pH 4 with acetic acid. The solid which separated was filtered off to give 2-nitroamino-5-(2-furylmethyl)-4-pyrimidone (17.1 g, 59%). A sample recrystallized from methanol-acetic acid and from acetic acid had m.p. 183°–184°.

EXAMPLE 8

Ethyl 2-formyl-3-(3-methoxyphenyl)propionate (10 g) was added dropwise to a stirred and boiling mixture of sodium methoxide (from 1.15 g sodium) and nitroguanidine (25% wet, 5.5 g) in methanol (250 ml) and the mixture was heated under reflux for 20 hours and evaporated to dryness. The residue was dissolved in water (100 ml), the solution was extracted with ether and the aqueous phase was adjusted to pH 4: the solid which separated was recrystallized from ethanol to give 2-nitroamino-5-(3-methoxybenzyl)-4-pyrimidone (3.41 g, 29%), m.p 178°–9°.

EXAMPLE 9

Crude ethyl 2-formyl-3-(3,4,5-trimethoxyphenyl)propionate (7.41 g) was reacted with nitroguanidine (2.62 g) and sodium methoxide in refluxing methanol for 40 hours to give 2-nitroamino-5-(3,4,5-trimethoxybenzyl)-4-pyrimidone in 13% yield.

EXAMPLE 10

A solution of ethyl 2-formyl-3-[5-(1,3-benzodioxolyl)]propionate (7.5 g) in methanol (20 ml) was added to sodium methoxide in methanol (prepared from 0.689 g sodium and 50 ml methanol); nitroguanidine (3.12 g) was then added to the stirred mixture. The mixture was heated under reflux for 18 hours and evaporated to a residue which was dissolved in water (200 ml) and the solution was extracted with chloroform. The residual aqueous phase was adjusted to pH 5 with acetic acid and the white solid which precipitated was filtered off to give 2-nitroamino-5-[5-(1,3-benzodioxolyl)methyl)]-4-pyrimidone (4.08 g), m.p. 200°–2°. A sample recrystallized from aqueous acetic acid had m.p. 201.5°–2.5°.

EXAMPLE 11

Nitroguanidine (11.10 g) was added to sodium methoxide (from 2.76 g sodium) in methanol (100 ml) and the mixture was heated under reflux for 45 min. Ethyl 2-formyl-3-[6-(2,3-dihydro-1,4-benzodioxinyl)]propionate (21.45 g) was added dropwise and the mixture was heated under reflux for 18 hours and evaporated to dryness. The residue was dissolved in water and the solution was extracted with chloroform. The residual aqueous phase was adjusted to pH 5 with acetic acid and the solid which precipitated was filtered off to give 2-nitroamino-5-[6-(2,3-dihydro-1,4-benzodioxinyl)-]methyl-4-pyrimidone (14.2 g, 58%), m.p. 194°–7°. A sample recrystallised from acetic acid had m.p. 207°–9°.

EXAMPLE 12

Nitroguanidine (9.10 g) was added to a solution of sodium methoxide (from 2.22 g sodium) in methanol (100 ml) and the mixture was heated under reflux for 45 minutes, ethyl-2-formyl-3-(1-naphthyl)propionate (16.05 g) was added and the mixture was heated under reflux for 20 hours and evaporated to dryness. The residue was poured into water and the mixture was extracted with chloroform and the pH of the residual aqueous phase was adjusted to 4 with acetic acid. The solid which precipitated was recrystallised from acetic acid to give 2-nitroamino-5-(1-naphthylmethyl)-4-pyrimidone, m.p. 226°–7°.

EXAMPLE 13

An intimate mixture of 2-(5-methyl-4-imidazolylmethylthio)ethylamine (0.86 g) and 2-nitroamino-5-(3-pyridylmethyl)-4-pyrimidone (1.24 g) was heated at 130°–5° for 11½ hours. The cool residue was washed with hot water, and then treated with hydrogen chloride in ethanol and the product recrystallised from ethanol-methanol to give 2-[2-(5-methyl-4-imidazolylmethylthio)ethylamino]-5-(3-pyridylmethyl)-4-pyrimidone trihydrochloride, m.p. 203°–5°, in 75% yield.

EXAMPLES 14 AND 15

Substitution of 3-(4-imidazolyl)propylamine and 4-(5-methyl-4-imidazolyl)butylamine, respectively, for the amine in the procedure of Example 1 using the same molar proportions of reagents gave 2-[3-(4-imidazolyl)propylamino]-5-(3-pyridylmethyl)-4-pyrimidone trihydrochloride, m.p. 208.5°–212° (Example 14), and 2-[4-(5-methyl-4-imidazolyl)butylamino]-5-(3-pyridylmethyl)-4-pyrimidone trihydrochloride, m.p. 242°–6° in 70% yield (Example 15).

EXAMPLE 16

A solution of 3-(5-methyl-4-imidazolylmethylthio)propylamine (1.64 g) and 2-nitroamino-5-(3-pyridylmethyl)-4-pyrimidone (1.97 g) in pyridine was heated under reflux for 20 hours, and the pyridine was removed by evaporation. The residue was crystallised from ethanol containing hydrogen chloride, and recrystallised from ethanol-methanol to give 2-[3-(5-methyl-4-imidazolylmethylthio)propylamino]-5-(3-pyridylmethyl)-4-pyrimidone trihydrochloride, m.p. 233°–6°.

EXAMPLES 17 TO 19

Using a procedure similar to that of Example 16, 2-nitroamino-5-(3-pyridylmethyl)-4-pyrimidone was reacted with 1.1 molar equivalents of 2-(4-methyl-2-pyridylmethylthio)ethylamine, 4-(3-chloro-2-pyridyl)butylamine, and 2-(4-methoxy-2-pyridylmethylthio)ethylamine, respectively, to give:

2-[2-(4-methyl-2-pyridylmethylthio)ethylamino]-5-(3-pyridylmethyl)-4-pyrimidone, m.p. 128°–9° (Example 17).

2-[4-(3-chloro-2-pyridyl)butylamino]-5-(3-pyridylmethyl)-4-pyrimidone, m.p. 146°–7.5° (Example 18).

2-[2-(4-methoxy-2-pyridylmethylthio)ethylamino]-5-(3-pyridylmethyl)-4-pyrimidone, m.p. 99°–100° (Example 19).

EXAMPLE 20

A mixture of 2-(3,4-dimethoxy-2-pyridylmethylthio)ethylamine (0.95 g, 4.16 mmol), 2-nitroamino-5-(3-pyridylmethyl)-4-pyrimidone (0.925 g, 3.74 mmol) and pyridine (3.5 ml) was heated under reflux for 24 hours and evaporated to dryness. The residue was purified by elution from silica gel with methanolchloroform (1:7) and recrystallisation from ethanol to give 2-[2-(3,4-dimethoxy-2-pyridylmethylthio)ethylamino]-5-(3-pyridylmethyl)-4-pyrimidone 121°–1.5°.

EXAMPLE 21

Using a procedure similar to that of Example 16, 2-nitroamino-5-(3-pyridylmethyl)-4-pyrimidone was reacted with 1.1 molar equivalents of 4-(3-amino-2-pyridyl)butylamine, to give 2-[4-(3-amino-2-pyridyl)butylamino]-5-(3-pyridylmethyl)-4-pyrimidone, m.p. 130°–1.5°.

EXAMPLE 22

When 2-nitroamino-5-(3-pyridylmethyl)pyrimidone in pyridine was heated under reflux for 16 hours with 1.5 molar equivalents of 3-(2-thiazolyl)propylamine, followed by isolation of the product, there was obtained 2-[3-(2-thiazolyl)propylamino]-5-(3-pyridylmethyl)-pyrimidone, m.p. 168°–172°.

EXAMPLE 23

When the same molar equivalent amount of 2-(2-thiazolylmethylthio)ethylamine was substituted for the amine in the procedure of Example 1, there was obtained 2-[2-(2-thiazolylmethylthio)ethylamino]-5-(3-pyridylmethyl)-4-pyrimidone trihydrochloride, m.p. 178°–180.5° in 76% yield.

EXAMPLE 24

A solution of 4-(3-methoxy-2-pyridyl)butylamine (5.48 g) and 2-nitroamino-5-(6-methyl-3-pyridylmethyl)-4-pyrimidone (7.95 g) in pyridine (200 ml) was heated under reflux for 18 hours and evaporated to dryness. The residue was extracted with warm propanol (200 ml) and the solution was acidified with ethanolic hydrogen chloride. The solid (10.83 g, 74%) which crystallised out was filtered off and recrystallised from propanol containing 1% 12N aqueous hydrochloric acid to give 2-[4-(3-methoxy-2-pyridyl)butylamino]-5-(6-methyl-3-pyridylmethyl)-4-pyrimidone trihydrochloride (7.53 g), m.p. 184°–8°.

EXAMPLE 25

A mixture of 5-(5,6-dimethyl-3-pyridylmethyl)-2-nitroamino-4-pyrimidone and 1.1 molar equivalents of 2-(5-methyl-4-imidazolylmethylthio)ethylamine was heated at 130° for 5 hours and heated under reflux in ethanol for 12 hours, evaporated to dryness and the product isolated as 2-[2-(5-methyl-4-imidazolylmethylthio)ethylamino]-5-(5,6-dimethyl-3-pyridylmethyl)-4-pyrimidone monohydrate, m.p. 115° (softening at 98°).

EXAMPLE 26

A mixture of 5-(5,6-dimethyl-3-pyridylmethyl)-2-nitroamino-4-pyrimidone and 1.2 molar equivalents of 2-(3-bromo-2-pyridylmethylthio)ethylamine was heated under reflux in ethanol for 48 hours, evaporated to dryness and the product isolated as 2-[2-(3-bromo-2-pyridylmethylthio)ethylamino]-5-(5,6-dimethyl-3-pyridylmethyl)-4-pyrimidone, m.p. 105°–7°.

EXAMPLE 27

Equimolar amounts of 5-(5,6-dimethyl-3-pyridylmethyl)-2-nitroamino-4-pyrimidone and 4-(3-methoxy-2-pyridyl)butylamine were heated together under reflux in ethanol for 24 hours. An additional 0.1 molar equivalent of the amine was added and the mixture was heated under reflux for a further 24 hours, evaporated to dryness and purified to give 2-[4-(3-methoxy-2-pyridyl)butylamino]-5-(5,6-dimethyl-3-pyridylmethyl)-4-pyrimidone dihydrate, m.p. 93°–94°.

EXAMPLE 28

An equimolar mixture of 2-nitroamino-5-(6-methoxy-3-pyridylmethyl)-4-pyrimidone and 2-(5-methyl-4-imidazolylmethylthio)ethylamine was heated under reflux in ethanol for 18 hours. The solid which crystallised out on cooling was recrystallised from ethanol to give 2-[2-(5-methyl-4-imidazolylmethylthio)ethylamino]-5-(6-methoxy-3-pyridylmethyl)-4-pyrimidone, m.p. 197°–8.5°, in 63% yield.

EXAMPLE 29

An equimolar mixture of 2-nitroamino-5-(6-methoxy-3-pyridylmethyl)-4-pyrimidone and 2-(2-thiazolylmethylthio)ethylamine was heated under reflux in ethanol for 18 hours. The solid which crystallised out on cooling was recrystallised from ethanol to give 2-[2-(2-thiazolylmethylthio)ethylamino]-5-(6-methoxy-3-pyridylmethyl)-4-pyrimidone, m.p. 95°–7°, in 60% yield.

EXAMPLES 30 AND 31

When 2-nitroamino-5-(2-methoxy-4-pyridylmethyl)-4-pyrimidone was heated under reflux in ethanol for 18 hours with equimolar amounts of 2-(5-methyl-4-imidazolylmethylthio)ethylamine and 2-(2-thiazolylmethylthio)ethylamine, respectively, isolation of the products gave 2-[2-(5-methyl-4-imidazolylmethylthio)ethylamino]-5-(2-methoxy-4-pyridylmethyl)pyrimidone, m.p. 177°–8° (Example 30), and 2-[2-(2-thiazolylmethylthio)ethylamino]-5-(2-methoxy-4-pyridylmethyl)-pyrimidone, m.p. 105.5°–6.5° (Example 31).

EXAMPLE 32

2-(2-Thiazolylmethylthio)ethylamine (2.00 g) and 2-nitroamino-5-(3-methoxybenzyl)-4-pyrimidone (1.58 g) were fused together at 130° for 4 hours. The mixture was triturated with hot water and the residue was recrystallised from 2-propanol to give 2-[2-(2-thiazolylmethylthio)ethylamino]-5-(3-methoxybenzyl)-4-pyrimidone (0.93 g), m.p. 122°–4°. A sample was treated with hydrogen chloride in ethanol and after recrystallision from isopropanol/methanol it had m.p. 104°–6° and gave analytical data corresponding to a hemihydrochloride.

EXAMPLE 33

2-Nitroamino-5-(3,4,5-trimethoxybenzyl)-4-pyrimidone (1.12 g) was fused with 2-(5-methyl-4-imidazolylmethylthio)ethylamine (0.65 g) at 130°–5° for 12 hours. The cool residue was washed with hot water and the residue was treated with hydrogen chloride in ethanol and recrystallised from ethanol to give 2-[2-(5-methyl-4-imidazolylmethylthio)ethylamino]-5-(3,4,5-trimethoxybenzyl)-4-pyrimidone dihydrochloride, m.p. 171°–4°.

EXAMPLE 34

A mixture of 2-(5-methyl-4-imidazolylmethylthio)ethylamine (1.54 g), 2-nitroamino-5-[5-(1,3-benzodioxolyl)methyl]-4-pyrimidone (2.5 g) and ethanol (20 ml) was heated under reflux for 24 hours. Hydrogen chloride in ethanol was added to the hot solution and 2-[2-(5-methyl-4-imidazolylmethylthio)ethylamino]-5-[5-(1,3-benzodioxolyl)methyl]-4-pyrimidone dihydrochloride (2.9 g) crystallised out on cooling. This product was dissolved in water and the solution was adjusted to pH 8 with aqueous sodium bicarbonate, and the free base was filtered off. The free base was recrystallised from ethanol containing hydrogen chloride to give a sample of the dihydrochloride with m.p. 232°–6°.

EXAMPLE 35

A mixture of 2-nitroamino-5-[6-(2,3-dihydro-1,4-benzodioxinyl)methyl]-4-pyrimidone (3.04 g), 2-(5-methyl-4-imidazolylmethylthio)ethylamine (1.92 g) and ethanol (20 ml) was heated under reflux for 21 hours and evaporated to dryness. The residue was washed with hot water and twice recrystallised from ethanol containing hydrogen chloride to give 2-[2-(5-methyl-4-imidazolylmethylthio)ethylamino]-5-[6-(2,3-dihydro-1,4-benzodioxinyl)methyl]-4-pyrimidone dihydrochloride, m.p. 210°–213°.

EXAMPLES 36 TO 38

Reaction of 2-(5-methyl-4-imidazolylmethylthio)ethylamine with equimolar amounts of
- 2-nitroamino-5-(4-methoxy-2-pyridylmethyl)-4-pyrimidone,
- 2-nitroamino-5-(2-furylmethyl)-4-pyrimidone and
- 2-nitroamino-5-(1-naphthylmethyl)-4-pyrimidone, respectively, gives:
- 2-[2-(5-methyl-4-imidazolylmethylthio)ethylamino]-5-(4-methoxy-2-pyridylmethyl)-4-pyrimidone (Example 36),
- 2-[2-(5-methyl-4-imidazolylmethylthio)ethylamino]-5-(2-furylmethyl)-4-pyrimidone (Example 37), and
- 2-[2-(5-methyl-4-imidazolylmethylthio)ethylamino]-5-(1-naphthylmethyl)-4-pyrimidone, isolated as the dihydrochloride, m.p. 228°–30° (Example 38).

Other compounds of Structure 1 which can be prepared from the nitroaminopyrimidones of Structure 3 by a process of the invention, for example compounds where Z is lower alkyl (for instance methyl) and where A is $(CH_2)_p W(CH_2)_q$ (for instance where A-B is benzyloxybenzyl), are described in German Offenlegungsschriften Nos. 2643670 and 2658267, and U.S. Pat. No. 3,932,644.

I claim:

1. A process for preparing a 2-aminopyrimidone of Structure 1

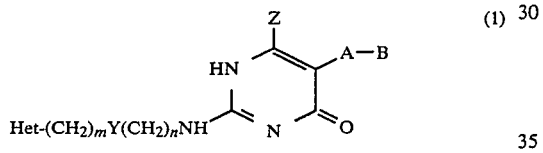

(1)

in which Het is a nitrogen-containing 5- or 6-membered fully unsaturated heterocyclic group selected from imidazolyl, pyridyl, thiazolyl, isothiazolyl, oxazolyl, isoxazolyl, triazolyl and thiadiazolyl which is optionally substituted by lower alkyl, trifluoromethyl, halogen, hydroxy, lower alkoxy or amino, m is 0 or 1, Y is methylene, oxygen or sulphur; n is 2 or 3; Z is hydrogen or lower alkyl; A is $C_1$–$C_5$ alkylene or —$(CH_2)_p$—$W(CH_2)_q$— where W is oxygen or sulphur and the sum of p and q is 1 to 4; and B is hydrogen, methyl, $C_3$–$C_6$ cycloalkyl, a heteroaryl group selected from pyridyl, furyl, thienyl, thiazolyl, oxazolyl, isothiazolyl, imidazolyl, pyrimidyl, pyrazinyl, pyridazyl, thiadiazolyl, quinolyl, isoquinolyl, 5,6,7,8-tetrahydroquinolyl, 1,3-dioxolopyridyl, benzimidazolyl and benzthiazolyl optionally substituted by lower alkyl or lower alkoxy, or B is a napthyl, 5- or 6-(2,3-dihydro-1,4-benzodioxinyl), or a 4- or 5- (1,3-benzodioxolyl) group, or a phenyl group optionally substituted with lower alkyl, lower alkoxy, halogen, aryl(-lower alkoxy), hydroxy, lower alkoxy-lower alkoxy, trifluoromethyl, di(lower alkyl)amino, phenoxy, halophenoxy, lower alkoxyphenoxy, phenyl, halophenyl or lower alkoxyphenyl; characterised in that an amine of Structure 2 is reacted with a 2-nitroaminopyrimidone of Structure 3.

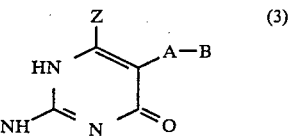

(3)

Het-$(CH_2)_m Y(CH_2)_n NH_2$   $NO_2NH$

2. A process according to claim 1, in which the reaction is carried out in refluxing ethanol, refluxing 1-propanol or refluxing pyridine.

3. A process according to claim 1 or claim 2, in which an excess of the amine of Structure 2 is used.

4. A process according to claim 1 or claim 2 in which the product prepared is
   (a) 2-[2-(5-methyl-4-imidazolylmethylthio)ethylamino]-5-(3-methoxybenzyl)-4-pyrimidone
   (b) 2-[2-(5-methyl-4-imidazolylmethylthio)ethylamino]-5-[5-(1,3-benzodioxolyl)methyl]-4-pyrimidone
   (c) 2-[2-(5-methyl-4-imidazolylmethylthio)ethylamino]-5-(3-pyridylmethyl)-4-pyrimidone
   (d) 2-[4-(3-methoxy-2-pyridyl)butylamino]-5-(6-methyl-3-pyridylmethyl)-4-pyrimidone, or
   (e) 2-[4-(3-methoxy-2-pyridyl)butylamino]-5-(3-pyridylmethyl)-4-pyrimidone.

5. A 2-nitroaminopyrimidone of the formula:

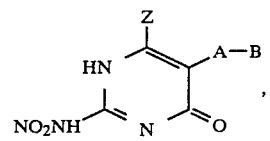

in which Z is hydrogen or lower alkyl, A is $C_1$–$C_5$ alkylene or —$(CH_2)_p W(CH_2)_q$— where W is oxygen or sulphur and the sum of p and q is 1 to 4, and B is a heteroaryl group selected from pyridyl, furyl, thienyl, thiazolyl, oxazolyl, isothiazolyl, imidazolyl, pyrimidyl, pyrazinyl, pyridazyl, thiadiazolyl, quinolyl, isoquinolyl, 5,6,7,8-tetrahydroquinolyl, 1,3-dioxolopyridyl, benzimidazolyl and benzthiazolyl optionally substituted by lower alkyl or lower alkoxy.

6. A 2-nitroaminopyrimidone according to claim 5, in which A is methylene.

7. A 2-nitroaminopyrimidone according to claim 5, in which Z is hydrogen.

8. A 2-nitroaminopyrimidone according to claim 5, claim 6 or claim 7, in which B is a pyridyl group.

9. A 2-nitroaminopyrimidone according to claim 5, claim 6 or claim 7, in which B is 3-pyridyl, 6-methyl-3-pyridyl, 5,6-dimethyl-3-pyridyl, 6-methoxy-3-pyridyl, 2-methoxy-4-pyridyl or 4-methoxy-2-pyridyl.

10. A 2-nitroaminopyrimidone according to claim 5, claim 6 or claim 7, in which B is a 2-furyl group.

* * * * *